United States Patent [19]

Snyder et al.

[11] Patent Number: 5,045,209

[45] Date of Patent: Sep. 3, 1991

[54] METHOD FOR CHROMATOGRAPHICALLY RECOVERING SCANDIUM AND YTTRIUM

[75] Inventors: Thomas S. Snyder, Oakmont, Pa.; Richard A. Stoltz, Plano, Tex.

[73] Assignee: Westinghouse Electric Corp., Pittsburgh, Pa.

[21] Appl. No.: 587,191

[22] Filed: Sep. 24, 1990

[51] Int. Cl.$^5$ .................................. B01D 15/08
[52] U.S. Cl. .......................... 210/656; 210/635; 210/198.2; 423/21.5; 423/658.5
[58] Field of Search .................. 423/21.1, 21.5, 658.5; 210/635, 656, 198.2

[56] References Cited

U.S. PATENT DOCUMENTS

| | | | |
|---|---|---|---|
| 3,167,389 | 1/1965 | Woyski | 423/21.5 |
| 4,394,353 | 7/1983 | Miyake | 210/674 |
| 4,411,793 | 10/1983 | Kato | 210/656 |
| 4,599,175 | 7/1986 | Yamamizu | 210/656 |
| 4,751,061 | 6/1988 | Kim | 423/21.5 |
| 4,902,426 | 2/1990 | Macedo | 210/656 |
| 4,965,053 | 10/1990 | Herchenroeder | 423/21.5 |
| 4,988,487 | 1/1991 | Lai | 423/21.5 |
| 4,995,984 | 2/1991 | Barkatt | 210/682 |

Primary Examiner—Ernest G. Therkorn
Attorney, Agent, or Firm—J. C. Valentine

[57] ABSTRACT

Scandium and yttrium present in sand is recovered from the residue pulled from sand chlorinators. The residue is digested with an acid to produce a liquid containing scandium, yttrium, sodium, calcium and at least one radioactive metal of the group consisting of radium, thorium and uranium. The metal-containing liquid is then fed through a cation exchanger. The cation exchanger is eluted with an acid to produce eluate functions containing at least partially separated metals. A first eluate fraction contains at least half of the calcium and the sodium, a second eluate fraction contains at least half of the radioactive metals, a third eluate fraction contains at least half of the scandium and a fourth eluate fraction contains at least half of the yttrium which were contained in the metal-containing feed.

10 Claims, 6 Drawing Sheets

METHOD FOR CHROMATOGRAPHICALLY RECOVERING SCANDIUM AND YTTRIUM

The invention relates to a method for chromatographically recovering scandium and yttrium in the residue from a sand chlorinator.

BACKGROUND OF THE INVENTION

In the production of such metals as zirconium, hafnium and titanium by Kroll reduction processes, zircon and rutile sands are first chlorinated in the presence of carbon to produce gaseous zirconium, hafnium, titanium and silicon tetrachlorides, which metals are then reduced with, e.g., magnesium. The sands are typically chlorinated in the presence of carbon at temperatures greater than about 800° C. in fluidized beds. Nonvolatile compounds, and particularly calcium and sodium salts, in the zircon and rutile sands eventually build up in the chlorinators and create "sticky" bed conditions which inhibit fluidization thus the residues in the chlorinators must be periodically pulled.

The zircon and rutile sands may also contain small amounts of other elements which are removed from the chlorinators in the residues. Thus the residues generally contain radium, scandium, yttrium and other transition metals, including metals from the rare earth and actinide series. Depending upon their compositions, these residues must be disposed of (at significant cost) as RCRA and low radioactive level wastes because of the presence of radioactive radium, thorium and uranium. Preferably, the volume of these wastes are minimized for permanent storage.

It has been recently proposed to recover scandium and yttrium from the chlorinator residues as saleable byproducts in order to recover at least some of the cost of disposing of the wastes. Yttrium is useful in advanced ceramics and superconductor applications. Scandium is useful in various laser applications. These proposals generally involve a rather complicated sequence of multistage solvent extractions and precipitations. Organic solvents may be employed to extract the metal values. Thus these proposed processes result in additional liquid waste streams which must be treated.

SUMMARY OF THE INVENTION

It is an object of the present invention to recover scandium and yttrium in the residues from chlorinators by a process which does not generate substantial liquid wastes. It is a further object to separate radioactive elements so that only minimum volumes of RCRA and low level wastes need to be buried.

With these objects in view, the invention resides in a method for chromatographically recovering scandium and yttrium from the residue of a sand chlorinator. A residue, which may be an accumulation of several batches, processed in accordance with the present invention generally contains scandium, yttrium, sodium, calcium and at least one radioactive metal of the group consisting of radium, thorium and uranium. The residue is digested with an acid, which is preferably hydrochloric acid, to produce a liquid containing these metals. The liquid is fed through a cation exchanger which adsorbs the metals. The cation exchanger is then eluted with an acid eluant to produce eluate fractions, including: a first eluate containing at least half of the total weight of the calcium and sodium in the feed liquid; a second eluate containing at least half of the total weight of the radioactive radium, thorium and uranium in the feed liquid; a third eluate comprising at least half of the yttrium in the feed liquid; and a fourth eluate containing at least half of the scandium in the feed liquid. Preferably, each eluate fraction contains at least 75% of the characterizing metal present in the feed liquid.

In a preferred practice, the cation exchanger moves, and most preferably continuously rotates, as it is fed with the metal-containing liquid and eluted with acid. In this practice of the present invention, the scandium, yttrium and the other metals and the acid eluant are separated and may be recovered in one simple process operation. In addition, one or more of the eluates may be concentrated and the concentrated eluates calcined to produce solid oxides. Where all of the metals are calcined, and the barren eluates and barren eluant recycled, the process advantageously produces zero liquid waste.

DESCRIPTION OF THE DRAWINGS

The invention will become more readily apparent from the following description of a preferred practice thereof shown, by way of example only, in the accompanying drawings, wherein.

DESCRIPTION OF THE PREFERRED EMBODIMENT

Figure 1:
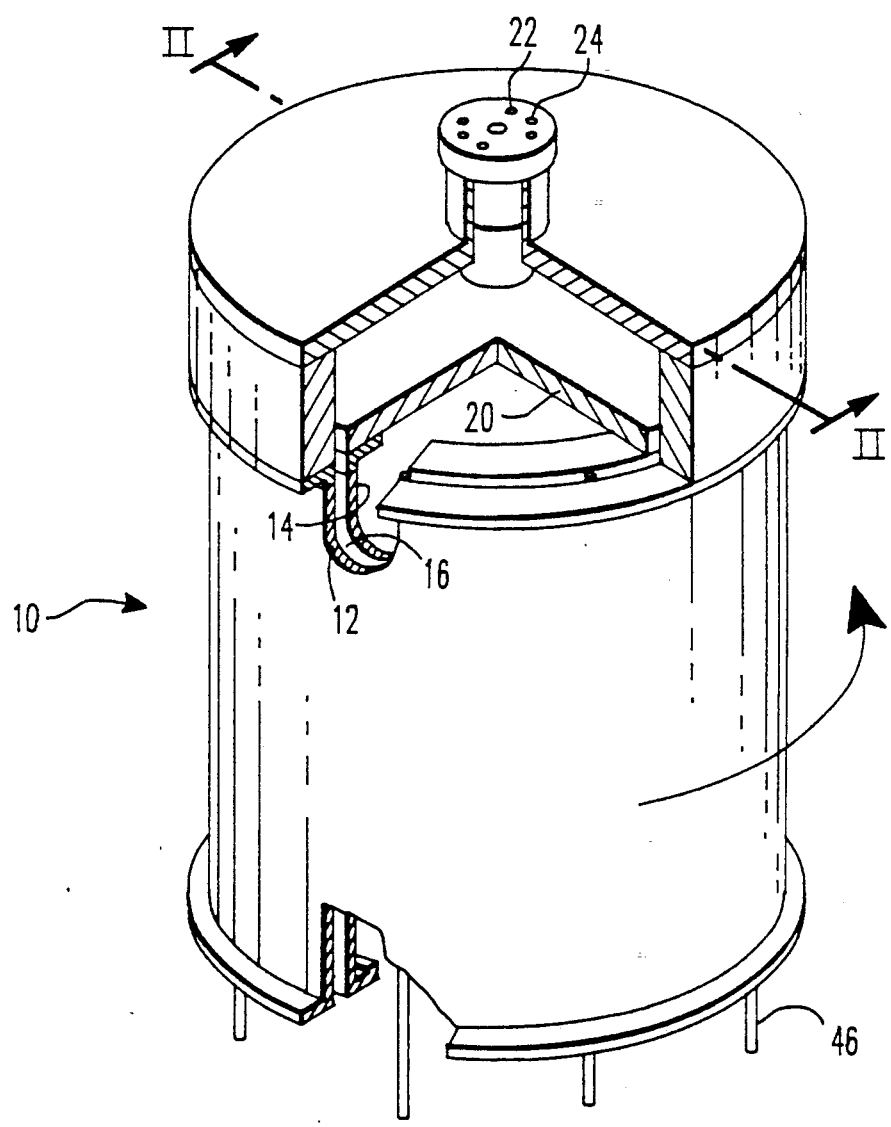
FIG. 1 is a perspective partially sectioned view of a cationic exchanger which may be employed in the practice of the present invention to chromatographically recover scandium and yttrium from a chlorinator residue.

FIGS. 1-5 generally show a cation exchanger 10 which may be advantageously employed to separately recover the scandium and the yttrium originally present in small amounts in sand which is chlorinated at temperatures over about 800° C.

The cation exchanger 10 is a known continuous annular chromatograph originally developed at Oak Ridge National Laboratories. Perry's Chemical Engineer's Handbook, Fourth Edition, McGraw-Hill Book Company, is hereby incorporated by reference for its discussion of the theory and design of such apparatus. The cation exchanger 10 of FIG. 1 generally comprises two concentric cylinders 12 and 14 which define an annular space 16 best seen in FIG. 2. Atop this annular space 16 is a distributor plate 20. Feed pipes or channels 22 and 24 run through the distributor plate 20 and terminate in feed nozzles 26 and 28, respectively. The feed nozzles 26 are intended to feed metal-containing liquid to resin beads 30 which are packed in the annular space 16. For ease of illustration, these resin beads 30 are shown as only partially filling the annular space 16. On the other hand, the feed nozzles 28 are intended to feed eluant to a layer of glass beads 32 superposed over the resin beads 30. Thus the feed nozzles 28 are shorter than the feed nozzles 26. This feed arrangement limits back mixing of the metal-containing feed into the eluant above it. The feeds then flow downwardly through the annular bed of beads in the annular space 16.

Figure 2:
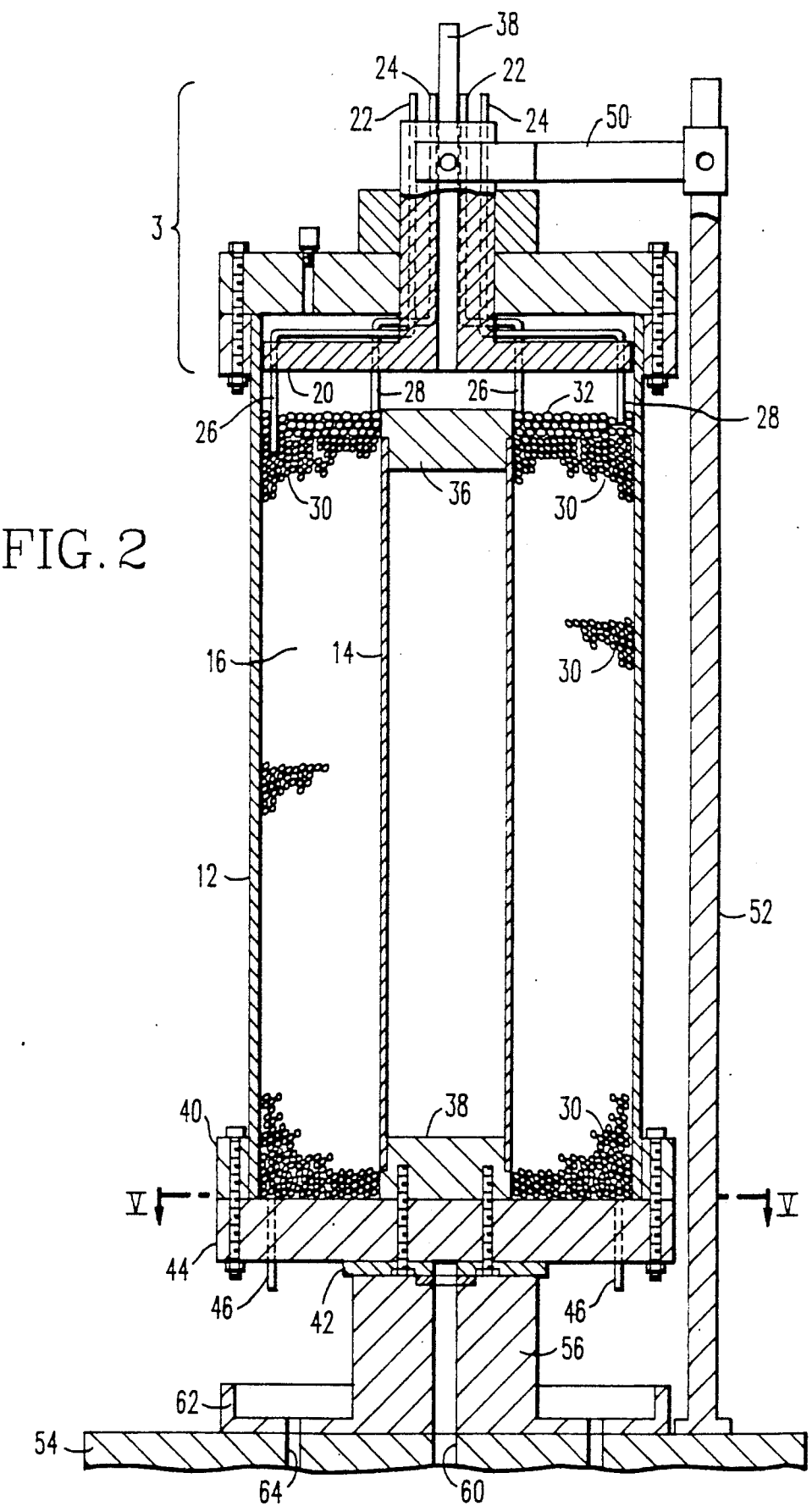
FIG. 2 is a horizontal sectional view of the cation exchanger of FIG. 1, generally taken along line 2—2.
Figure 3:
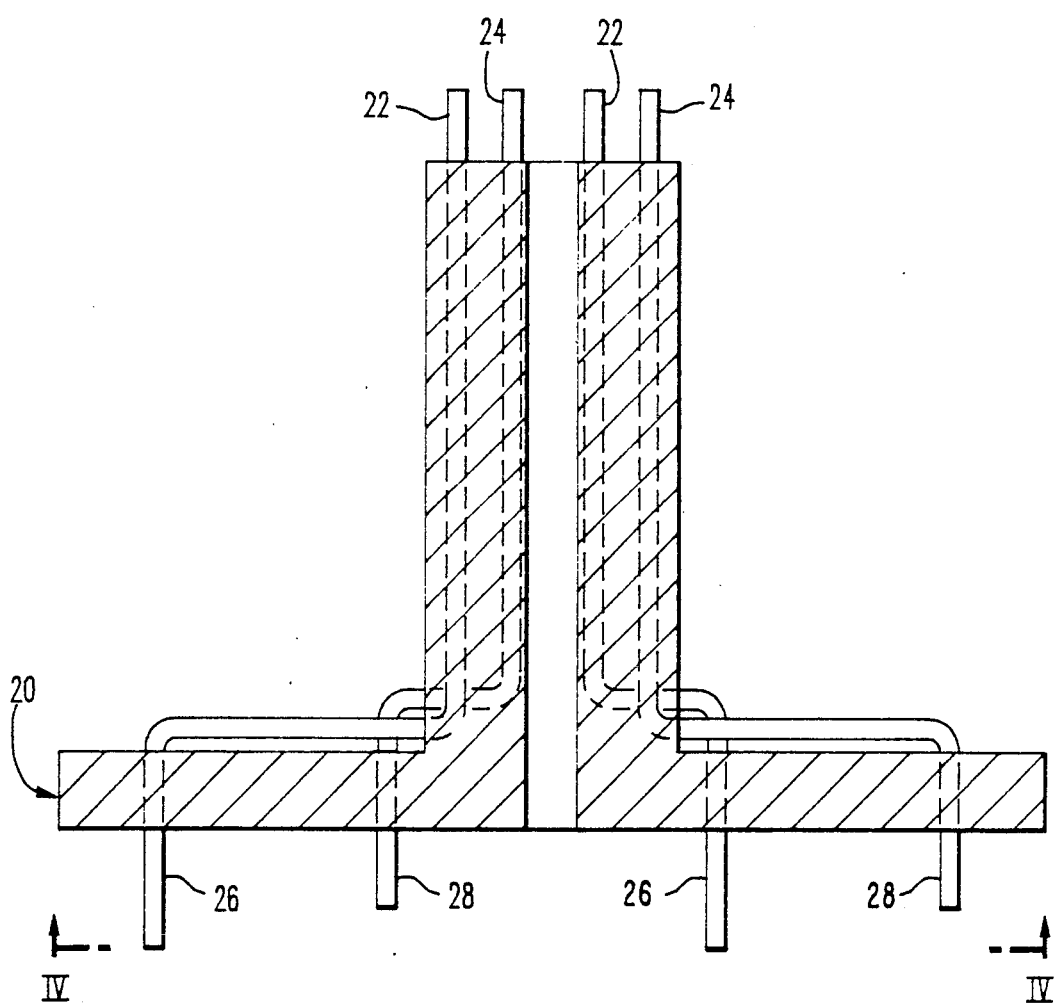
FIG. 3 is an enlarged horizontal sectional view of a part of the top portion of the cation exchanger of FIG. 1, generally enclosed by parenthesis 3 on FIG. 2.
Figure 4:
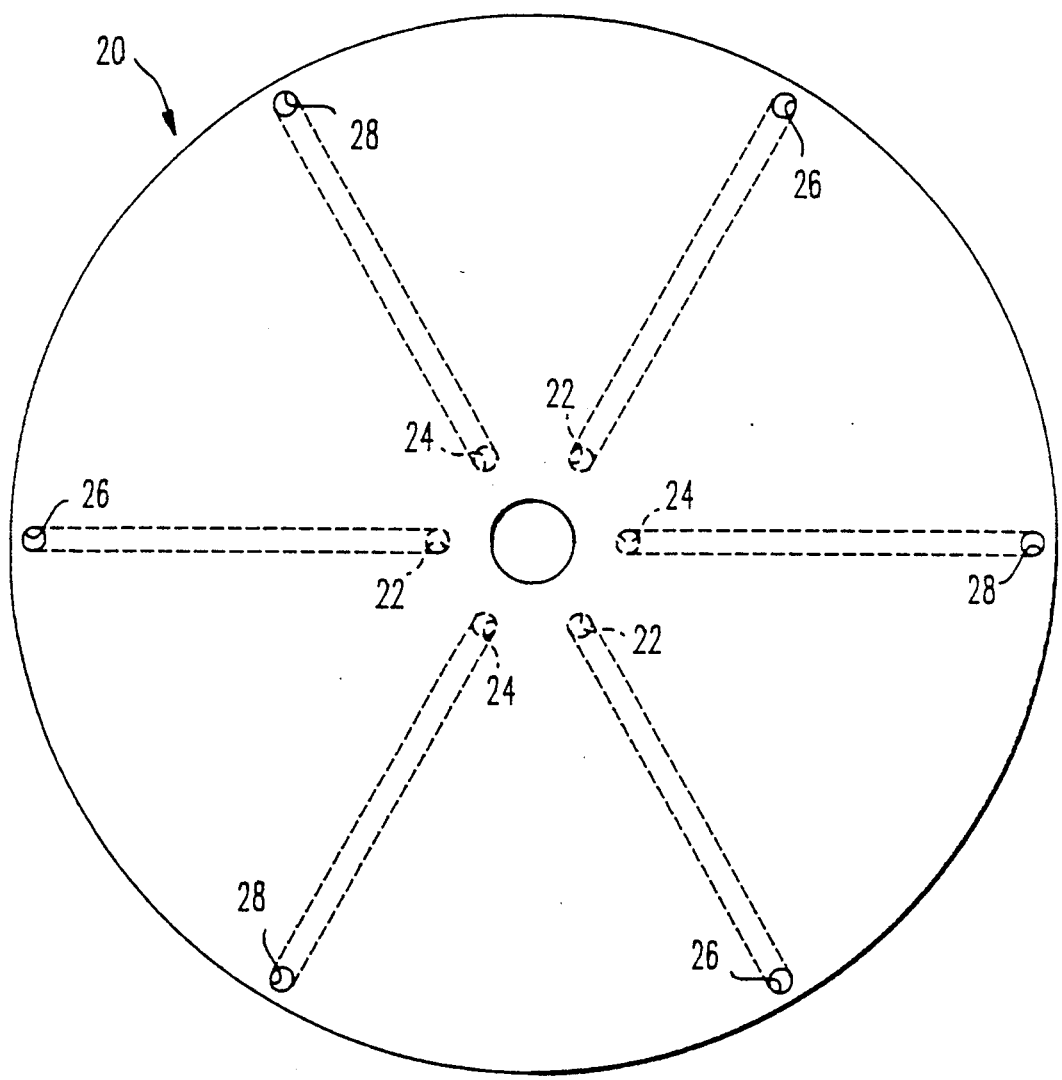
FIG. 4 is an enlarged plan view of the structure shown in FIG. 3.
Figure 5:
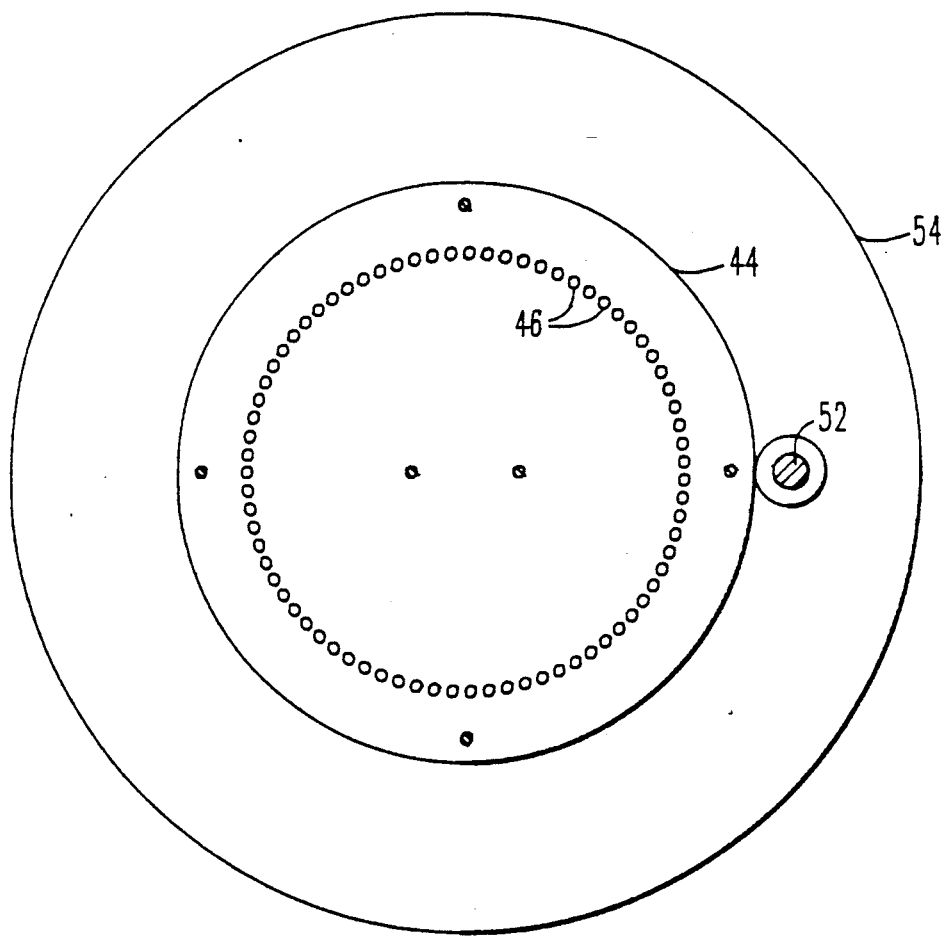
FIG. 5 is a plan view of the bottom of the cation exchanger of FIG. 1, taken along line 5—5 of FIG. 2.

The central cavity defined by the inner cylinder 14 is sealed by an upper cap 36 so that a pipe 38 can be used to apply pressure to the annular bed of beads. A lower cap 38 in the central cavity and an outer collar 40 are bolted to a bottom plate for supporting the concentric cylinders 12 and 14 and the annular bed of beads. As is shown in FIG. 2, the lower cap 38 may be bolted to a mounting plate 42 through the bottom plate 44. As is best seen in FIG. 5, a large number of eluant delivery pipes 46 pass through this plate 44. This allows the collection of a variety of eluate fractions and also facilitates adjustments to the operating conditions to allow eluate collection at various angular displacements.

The distributor plate 20 is held in a fixed position above the annular space 16 by a bracket 50 which is turn connected to a support rod 52 which is affixed to a base plate 54. Also affixed to this base plate 54 is a support column 56 on which the bottom plate 44 rotatably rests. A shaft 60 passes through this support column 56 and base plate 54 and connects the mounting plate 42 to a motivating means not shown. Also affixed to the base plate 54 is an annular collection trough 62 which can be subdivided into any number of convenient segments, each with its own exit port 64.

The cation exchanger 10 is operated by rotating the annular space 16 packed with the resin beads 30 and the glass beads 32 beneath the fixed distributor plate 20 and its associated feed nozzles 26 and 28. The rotational force is supplied by the shaft 60. The cation exchanger 10 is typically rotated at a constant speed so that any vertical segment of the annular bed is above a particular fixed eluate delivery pipe 46 at a given time after this segment has been loaded with feed liquid and eluant. Thus, each eluate delivery pipe 46 has an angular position which corresponds to a particular elution time for a particular rate of rotation of the cation exchanger 10 and for a particular flow rate through the annular bed.

The flow rate through the annular bed essentially depends upon the pressure drop therethrough. The pressure drop may be solely due to the hydrostatic bead of liquid, but preferably the annular bed is also pressurized via pipe 38. The flow rate also depends upon the nature of the resin beads 30. A smaller average particle size requires a larger pressure drop to obtain a constant flow rate. However, the separation factor for any given theoretical stage is improved as the average particle size of the resin beads 30 is decreased. Thus, the effective bed height needed to effect a given degree of separation is decreased by decreasing the average particle size of the resin beads 30. Strong acid resins having mean diameters of about 0.01 to about 10 microns which are marketed under the designations AG50 wx 8 or Dowex 50×8 may be employed as resin beads 30.

The flow rate down the bed of resin beads 30 and the rotational speed of the cation exchanger 10 should be coordinated such that a particular eluate fraction always eluates at the same angular position and thus is always delivered to the same eluted delivery pipe 46.

It is preferred that the cation exchanger 10 be operated such that no more than about 5 percent, and more preferably no more than about 1 percent, of its exchange capacity is loaded with feed liquid before elution is initiated. This is conveniently effected by using a feed liquid which has insufficient acid strength to release the cations from ionic bonding with the cation exchange resin and loading no more than about 5 percent, and preferably about 1 percent, of the bed height with the feed liquid before adding an eluant of sufficient strength to cause the cations to migrate down the column at a reasonable rate. The angular displacement between the liquid feed nozzles 26 and the eluant nozzles 28 and the speed of rotation of the annular bed are designed so that the time interval between loading and elution is just sufficient to realize the desired degree of penetration. The relationship between the time for loading and the depth of penetration is determined by the flow rate through the annular bed.

The displacement of metal down the bed may be effected by either an isocratic or a gradient supply of eluant. In the former case, the eluant can simply be supplied from a single nozzle 28 while in the latter case, several nozzles 28 at successively greater angular displacements from the feed port are utilized. The ion exchanger 10 of FIG. 1 is designed for an isocratic elution mode. In the gradient mode, elution under the influence of the initial eluant is permitted to proceed until some separation of the cations has been effected and then a higher acid strength eluant is supplied. This increases the migration speed of the cations down the column and minimizes the range of elution volumes or times over which a given eluate fraction will exit the column or, in other words, this procedure minimizes the band spreading. Decreasing the elution volumes by gradient elution or by other means increases the cation concentration in the eluate fraction. Concentrations from about 0.1 to 50 gm/liter are preferred.

Figure 6:
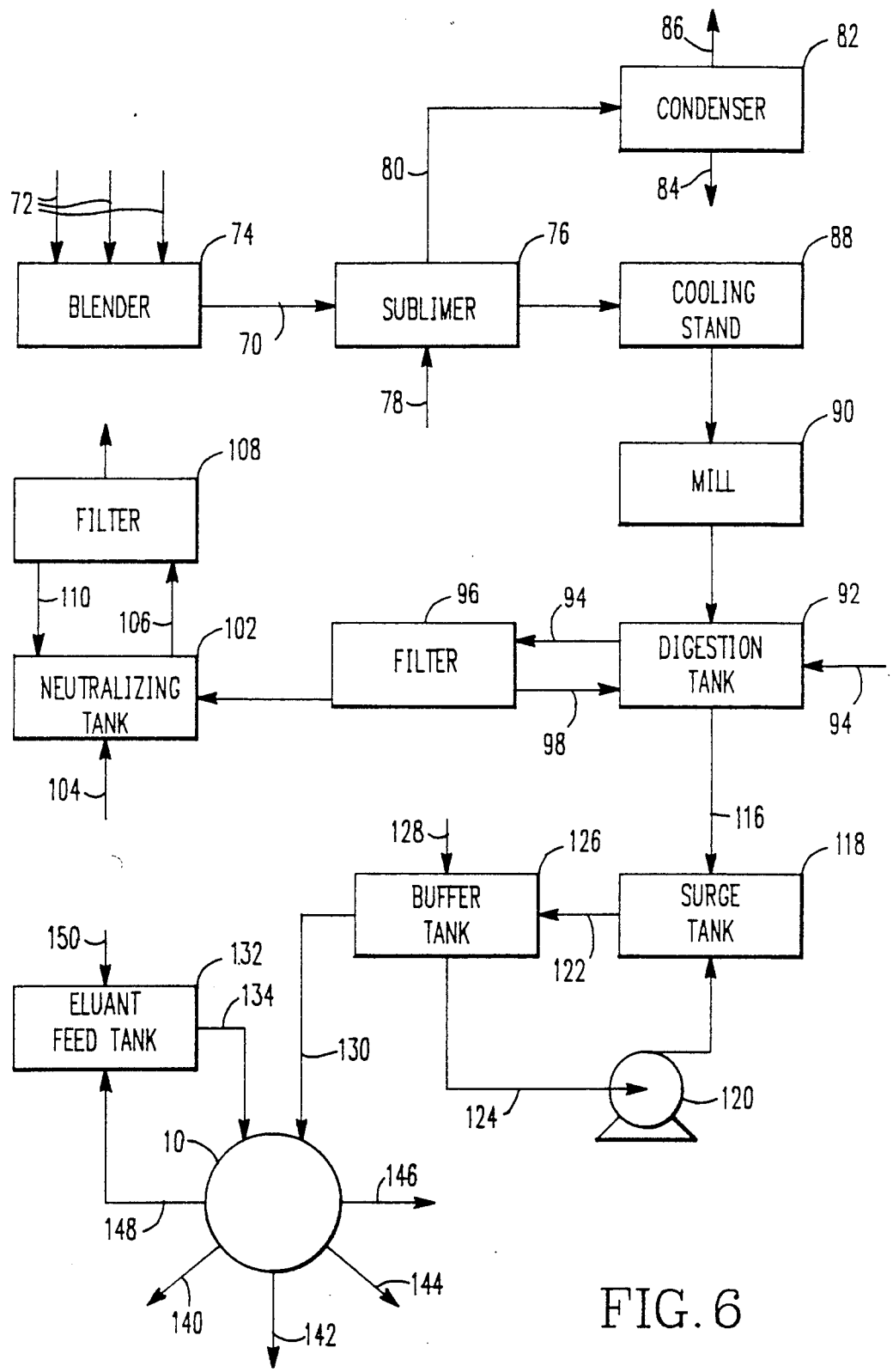
FIG. 6 is a flow sheet which illustrates the preferred practice of the present invention employing the cation exchanger of FIGS. 1-5.

FIG. 6 is a flow sheet depicting a process embodying the present invention for separating scandium and yttrium from a residue from a sand chlorinator (not shown). The process is designed to treat residues from a zircon sand chlorinator in a plant designed to produce zirconium and hafnium and will be described in that context. A similar process may be employed to treat residues from a rutile sand chlorinator in a titanium plant.

The residue 70, which may be (but usually would not be) a continuous process stream, is shown as an accumulation of batches 72 which are periodically pulled from one or more sand chlorinators. The batches 72 are blended in a blender 74 to provide a reasonably consistent feed to the recovery process. Generally speaking, the residue 70 contains unreacted coke, unreacted zirconium silicate, zirconium tetrachloride, hafnium tetrachloride, scandium, yttrium, calcium and sodium salts, and radioactive metals of the group radium, thorium and uranium. The residue may also contain small amounts of transition metals, including rare earth metals and actinide series metals. The composition of residues in a operating plant will vary considerably. A partial analysis of residue batches is shown in the following table:

| Element | Concentration Range (μg/gram) | Activity Range (pico Ci/gram) |
|---|---|---|
| Scandium | 2400–4300 | — |
| Yttrium | 28,000–40,000 | — |
| Uranium, all isotopes | 7–263 | — |
| Radium 226 | — | 1300–7000 |
| Radium 228 | — | 250–2090 |
| Thorium 228 | — | 1–20 |
| Thorium 230 | — | 5–40 |

| Element | Concentration Range (ug/gram) | Activity Range (pico Ci/gram) |
|---|---|---|
| Thorium 232 | — | 1-10 |

The residue 70 is fed to a sublimer 76, which may be a fluid bed, where residual zirconium tetrachloride and hafnium tetrachloride is sublimed off at a temperature of about 350° C. or more using chlorine-nitrogen mixtures from a line 78. The sublimed gases are fed by a line 80 to a condenser 82 where the hafnium tetrachloride and the zirconium tetrachloride are condensed and recycled by a line 84 to the next process step which is downstream of the chlorination step. The chlorine and nitrogen from the condenser 82 are recycled by a line 86 to, e.g., the zircon sand chlorinators (not shown). The residue from the sublimer 76 is cooled with air or other means at a cooling stand 88 (which may be the fluid bed sublimer 76) and then milled by any suitable milling apparatus 90 to maximize the surface area of the residue before digesting the residue.

The milled residue is digested in a digestion tank 96 with a strong acid from line 94 to dissolve the sodium and calcium; scandium, yttrium and other transition metals; and radium and other radioactive metals into a supernatant liquid over undigested coke and zirconium silicate. The digesting acid may be hydrochloric acid, nitric acid, sulfuric acid or mixtures thereof. The concentration of the acid is preferably about 1-6 molar, most preferably, the digesting acid is 3-6 molar hydrochloric acid. Strong acids at these concentrations will digest the residue in a reasonable time.

The contents of the digestion tank 92 are circulated through a line 94 by a pump (not shown) to a filter 96 which filters the undigested solids from supernatant liquid. The filtrate is recycled through a line 98 to the digestion tank 92. The undigested solids are fed to a neutralizer tank 102 where they are neutralized with a mild caustic from a caustic line 104. The neutralized solids are pumped through line 106 to a filter 108 which filters the undigested solids from the caustic. The undissolved solids are recycled to the zircon sand chlorination step. The filtrate is recycled through line 110 to the neutralizer tank 102.

The metal-containing supernatant liquid in the digestion tank 92 is a hydrochloric acid solution at a concentration of 3 molar or more in the preferred practice depicted in FIG. 6. The liquid must be buffered to a lower concentration before being fed to the cation exchanger 10. Thus supernatant liquid in the digestion tank 92 is fed through a line 116 to a surge tank 118. The liquid in the surge tank 118 is recirculated by a pump 120 through lines 122 and 124 to a buffer tank 126 where the liquid is buffered with a dilute acid fed through line 128 into the buffer tank 126 prior to introduction into the cation exchanger 10. The dilute acid may be any of the acids employed to digest the residue. Preferably the dilute acid is dilute hydrochloric acid in amounts sufficient to reduce the feed liquid to the cation exchanger 10 to a strength of 1-2 molar.

The buffered feed liquid is fed through line 130 into the cation exchanger 10. The eluant is fed from a feed tank 132 through line 134 into the cation exchanger 10. The eluant may be hydrochloric acid, nitric acid, sulfuric acid or mixtures thereof. Preferably the eluant is about 4-6 molar hydrochloric acid. If the cation exchanger 10 is operated in the gradient mode, several hydrochloric acid streams at increasing strength, e.g., a first stream at 4 molar concentration followed by a second stream at 5 molar concentration, are fed into the cation exchanger behind the liquid feed nozzle (or nozzles).

The metals in the feed liquid 130 separate in the cation exchanger 10 as they migrate through the cation resin bed 30 (shown in FIG. 2) and appear in different eluate fractions. A first eluate in line 140 is a hydrochloric acid solution containing at least half of the total weight of the calcium and the sodium in the feed stream 130. A second eluate in line 142 is a hydrochloric acid solution containing at least half of the total weight of the radioactive metals in the feed stream. A third eluate in line 144 is a hydrochloric acid solution containing at least half of the weight of the yttrium in the feed stream 130. A fourth eluate in line 146 is a hydrochloric acid solution containing at least half of the weight of the scandium in the liquid feed stream 130. A fifth eluate in line 14B comprising hydrochloric acid essentially stripped of all metals may be separately recovered and recycled to, e.g., the eluant feed tank 132 or to the buffer tank 126. If the fifth eluate is fed to the eluant feed tank 132 as shown in FIG. 6, then makeup eluant from line 150 will periodically be necessary to adjust the concentration of the eluant.

The separated metals may be sold or further treated before sale or final disposal. For example the eluates containing the calcium, sodium, radioactive metals, yttrium and scandium may be concentrated by distilling the eluant. The metals may then be calcined and then recovered as oxides. If the eluate containing sodium and calcium and the eluate containing radioactive materials are calcined there will be no liquid wastes to store and the waste volume which must be permanently disposed of, will be minimized. If the eluates containing the yttrium and the scandium are concentrated and calcined as well, there will be no liquid products or wastes which must be handled.

What is claimed is:

1. A method for chromatographically recovering scandium and yttrium from the residue of a sand chlorinator, comprising the steps of:
   providing a residue from a sand chlorinator, the residue containing scandium, yttrium, sodium, calcium and at least one radioactive metal of the group consisting of radium, thorium and uranium;
   digesting the residue with an acid to produce an aqueous liquid containing scandium, yttrium, sodium, calcium and at least one radioactive metal of the group consisting of radium, thorium and uranium;
   feeding the metal containing liquid through a cation exchanger;
   eluting the cation exchanger with an acid eluant to produce:
   a first eluate containing at least half of the total weight of the calcium and sodium in the feed liquid;
   a second eluate containing at least half of the total weight of the one or more radioactive metals in the feed liquid;
   a third eluate containing at least half of the yttrium in the feed liquid, and
   a fourth eluate containing at least half of the weight of the scandium in the feed liquid.

2. The chromatographic recovery method of claim 1, wherein the residue is digested with an acid selected from the group consisting of hydrochloric acid, nitric acid, sulfuric acid and mixtures thereof.

3. The chromatographic recovery method of claim 1, wherein the residue is digested with 3-6 molar hydrochloric acid.

4. The chromatographic recovery method of claim 3, wherein the metal-containing liquid is buffered with dilute hydrochloric acid to produce a 1-2 molar solution before it is fed through the cation exchanger.

5. The chromatographic recovery method of claim 1, wherein the cation exchanger is eluted with an acid selected from the group consisting of hydrochloric acid, nitric acid, sulfuric acid and mixtures thereof.

6. The chromatographic recovery method of claim 5, wherein the cation exchanger is eluted with 4-6 molar hydrochloric acid.

7. The chromatographic recovery method of claim 1, comprising the additional steps of:
   moving the cation exchanger as it is fed with metal-containing liquid and eluted with acid eluant.

8. The chromatographic recovery method of claim 7, wherein the cation exchanger continuously moves as it is fed and eluted.

9. The chromatographic recovery method of claim 7, wherein the cation exchanger is continuously rotated as it is fed and eluted.

10. The chromatographic recovery method of claim 1, comprising the additional steps of:
   concentrating at least one of the eluates to produce a concentrated metal eluate and a recyclable acid; and
   calcining the concentrated metal eluate to recover the metal as an oxide.

* * * * *